United States Patent [19]

Witte et al.

[11] 4,131,334
[45] Dec. 26, 1978

[54] LIGHT POLARIZING MATERIALS, SUSPENSIONS THEREOF, AND PROCESS FOR MANUFACTURING SUCH SUSPENSIONS

[75] Inventors: Michael Witte, Chatham, N.J.; Robert L. Saxe, New York; Robert I. Thompson, Plainview, both of N.Y.

[73] Assignee: Research Frontiers Incorporated, Plainview, N.Y.

[21] Appl. No.: 795,820

[22] Filed: May 11, 1977

[51] Int. Cl.² .......................... G02B 5/30; G02F 1/01
[52] U.S. Cl. ...................................... 350/147; 350/150
[58] Field of Search ................................. 350/147, 150

[56] References Cited

U.S. PATENT DOCUMENTS

| 1,955,923 | 4/1934 | Land | 350/151 |
| 3,989,639 | 11/1976 | Yaguchi et al. | 350/150 |

*Primary Examiner*—John K. Corbin
*Assistant Examiner*—R. A. Rosenberger
*Attorney, Agent, or Firm*—Jacobs & Jacobs

[57] ABSTRACT

An aliphatically unsaturated organic compound is hydrogenated to form a saturated compound and a salt of the saturated compound is reacted with a halogen and a halide to form a light-polarizing material. The light-polarizing material in the form of crystalline particles is dispersed in a suitable suspending medium to produce a fluid suspension thereof. The suspension is useful in light valves.

19 Claims, No Drawings

LIGHT POLARIZING MATERIALS, SUSPENSIONS THEREOF, AND PROCESS FOR MANUFACTURING SUCH SUSPENSIONS

FIELD OF THE INVENTION

This invention relates to light-polarizing materials and especially to such materials which are formed from saturated organic compounds derived or derivable from related unsaturated substances. This invention also relates to suspensions of such materials and methods of preparing them.

BACKGROUND OF THE INVENTION

There has been a need to increase the stability of polarizing materials against degradation due to heat and chemical exposure, in order thereby to produce superior polarizing materials. These materials, preferably in the form of colloidal particles, can be employed as the suspended material in a fluid suspension for use as the working material in a light valve.

Light valves incorporating fluid suspensions have been known for many years. Fluid suspensions of herapathite in a suitable liquid have heretofore been commonly preferred, although other types of particles have been suggested. In general, the shape of the particles used in such a light valve should be such that in one orientation they intercept more light than in another orientation. Particles which are needle-shaped, rod-shaped, lathshaped, or in the form of thin flakes, have been suggested. The particles may variously be light-absorbing or light-reflecting, polarizing, birefringent, metallic or non-metallic, and the like. In addition to herapathite, many other materials have been suggested such as graphite, mica, garnet red, aluminum, periodides of alkaloid sulphate salts, etc. Preferably, dichroic, birefringent or polarizing crystals are employed.

Very finely divided or minute particles, preferably collidal, are employed and are suspended in a liquid in which the particles are not soluble, and which is of suitable viscosity and relatively high electrical resistivity. In order to help stabilize the suspension when in the non-actuated state, a protective colloid, preferably a polymer, should be used to prevent agglomeration or settling.

Both electric and magnetic fields have been suggested for aligning the particles, although electric fields are more common. To apply an electric field, conductive area electrodes are provided on a pair of oppositely disposed walls of the cell, and an electric potential applied thereto. The electrodes may be thin transparent conductive coatings on the inner sides of the front and rear walls of the cell, thereby forming an ohmic type cell wherein the electrodes are in contact with the fluid suspension. It has also been suggested to cover the electrodes with a thin layer of transparent material such as glass in order to protect the electrodes. Such thin layers of glass form dielectric layers between the electrodes and the fluid suspension, and the cells may be termed capacitive cells. Direct, alternating and pulsed voltages have been applied to the electrodes in order to align the particles in the fluid suspension. When the voltage is removed, the particles return to a disoriented random condition due to Brownian movement.

Commonly the front and rear walls of the cell are transparent, for example, panels of glass or plastic. With no applied field, and random orientation of the particles, the cell has a low transmission to light and accordingly is in its "closed" condition. When a field is applied, the particles become aligned and the cell is in its "open" or light-transmitting condition. Instead of making the rear wall transparent, it may be made reflective or a reflective layer may be placed behind it. In such case light is absorbed when the cell is unenergized and is reflected when the cell is energized. These principal actions may be modified by employing light-reflecting rather than light-absorbing particles.

As aforesaid, one of the most common materials heretofore used in light valve suspensions is herapathite as disclosed in the Land patents, U.S. Pat. No. 1,951,664 and U.S. Pat. No. 1,955,923. Herapathite is quinine bisulfate periodide, the formula for which is stated in the Merck Index (Eighth Edition) as $4C_{20}H_{24}N_2O_2.3H_2SO_4.2HI.I_4.6H_2O$. The Merck Index is published by Merck & Co., Inc., Rahway, N.J. Herapathite, although an effective polarizing material, is not stable either to heat or to small or even trace amounts of certain types of chemicals. Because, in many uses, suspensions are subject to exposure to either or both the aforesaid conditions, it is important and usually essential that the particles and suspension not be subject to degradation due to heat or exposure to chemicals during or after their formation.

It is particularly important to avoid deterioration of particles and suspension, so that the suspension can be used as the working material in light valves. For example, it has been observed that a suspension of herapathite particles suspended in isopentyl acetate liquid or other similar liquid esters, together with the polymer nitrocellulose which is used to help keep the particles suspended in the manner of the prior art, will change color from blue initially to red-purple after a period of several months, even at room temperature. At higher temperatures the color degradation may be even more severe and takes place much more rapidly.

Also, in order to prepare a suspension of herapathite or the improved materials of this invention, the particles must be prepared in the presence of a solvent, some of which solvent may remain in trace amounts in the final fluid suspension. If such chemical solvents degrade the suspended particles, as is evidenced, for example by a color change or a loss in the optical density of the suspension, the particles and suspension are unlikely to be commercially usable over a long period of time. Accordingly, herapathite has limitations for its use in a light valve suspension because it partially decomposes when in contact with common solvents such as methanol, and 2-ethoxyethanol, which solvents or others similar to them are often necessarily present during particle formation. Degradation products of nitrocellulose such as nitrous acid also seem to attack herapathite.

SUMMARY OF THE INVENTION

A saturated organic compound, such as a dihydro-organic material is formed by saturating, e.g., hydrogenating an aliphatically unsaturated organic compound, and a salt of the saturated compound is then produced. The organic salt is then reacted with other mateials to form a light-polarizing material. For example, cinchonidine, $C_{19}H_{22}N_2O$, which includes an aliphatically unsaturated double bond, is converted by hydrogenation to the saturated compound, dihydrocinchonidine, which in turn may be reacted with other materials to form a salt such as, dihydrocinchonidine sulfate. The latter is then reacted with a halogen and a halide, usually iodine and an iodide respectively to form the polarizing material. The resulting compound in this instance could be, for example, dihydrocinchonidine sulfate calcium iodide periodide, if calcium iodide is chosen as the aforesaid iodide. Because many iodides other than calcium iodide can be used in its place, a compound of this general type may be referred to simply as dihydrocinchonidine sulfate periodide. The compound, dihydrocinchonidine sulfate periodide has superior effectiveness as a polarizing material for use in suspensions, relative to either herapathite or cinchonidine sulfate periodide, because it is found to be more resistant to degradation from heat and chemicals. Other unsaturated organic compounds besides cinchonidine may be similarly treated to obtain similarly improved stability, as will be elaborated hereinafter. A method is described for preparing a fluid suspension that includes particles of the polarizing material, the suspension being suitable for use in a light valve.

It is thus an object of this invention to provide a polarizing material for use in light valve suspensions which is capable of withstanding deterioration from the effect of heat.

It is a further object of this invention to provide a polarizing material for use in light valve suspensions that is able to withstand degradation from the effect of lower alcohols and ether-alcohols.

It is a further object of this invention to form a polarizing material by first reducing a suitable aliphatically unsaturated organic material to form a saturated compound, then forming a suitable salt of said saturated compound, and then reacting said salt with an iodide and iodine, or the corresponding bromine compounds or an iodide and bromine, or a bromide and iodine, to form periodide or the corresponding perbromide or related particles therefrom.

It is another object of this invention to make a fluid suspension for a light valve that incorporates such a suspended polarizing material.

It is a further object of this invention to provide a process for making such a fluid suspension.

DESCRIPTION OF THE INVENTION AND PREFERRED EMBODIMENT

This invention relates to light-polarizing materials are particularly to materials which can comprise the suspended particles in suspensions, e.g., colloidal suspensions for use in fluid suspension light valves. The suspended material in such a fluid suspension must be able to withstand the effects of contact with various chemicals, specifically lower alcohols and ether-alcohols, and such material and suspensions thereof should be able to withstand exposure to temperatures substantially above room temperature for a reasonably long period of time.

We have found that light polarizing particles and suspensions thereof can be produced which meet these objectives, by following the methods and using the materials hereinafter described.

The particles of the present invention are light-polarizing perhalide particles, preferably periodide (polyiodide) particles. In order to describe the polarizing materials fully, the general procedure by which they can be produced shall be stated first, after which specific examples and details shall be given.

The general process for forming the particles is as follows. A suitable unsaturated organic material, called the "base material," is reduced, for example by hydrogenation, so as to saturate the material. The resulting reduced material is called the "starting material." The starting material is then reacted with an appropriate acid to form a salt, called the "precursor." The precursor is then dissolved in an appropriate liquid medium, and, preferably in the presence of a polymeric protective colloid, is then reacted with effective amounts of a halogen element and a halide to produce perhalide particles.

Many suitable base materials can be employed in the present invention. Indeed, as a non-limiting but easy method of determining suitable base materials, any organic compound having an unsaturated bond which bond when hydrogenated, and a salt form thereof is reacted with a halide and a halogen to form a perhalide which is light-polarizing is a suitable material. Suitable examples include the alkaloids such as derivatives of quinoline. An example is quinine. Another example is cinchonidine.

It is to be noted that the unsaturated bond may be present in the alpha-position of the branch chain of an aryl group.

However, in some instances we have found that light-polarizing particles can be formed by reacting the sulfate salt of the reduced base material (i.e., starting material) with iodine and an iodide, even though we were unable to form light-polarizing particles by similarly reacting the sulfate salt of the unreduced base material. Examples of such base materials include quinidine and cinchonine.

In the examples cited in the previous paragraph, sulfate salts are mentioned. These are salts formed by reacting an (unsaturated) base material or a (saturated) starting material with sulfuric acid, an inorganic acid. Sulfuric acid, however, is not the only appropriate acid usable in forming light-polarizing perhalide particles including the materials of the present invention. It has been found that polybasic organic acids, and hydroxy and polyhydroxy polybasic acids, are also appropriate for such use. Examples of such organic acids include mucic acid, terephthalic acid, and pyromellitic acid, although it should be appreciated that a vast number of other acids would also be appropriate, provided that they meet the aforesaid criteria.

In Example 1 a process is described for reducing an (aliphatically unsaturated) base material, namely cinchonidine, to form a (saturated) starting material. The reduction is accomplished by hydrogenation, although it will be appreciated that other known methods of saturating the aliphatically unsaturated portion of the cinchonidine molecule, might also be employed.

EXAMPLE 1

Preparation of Dihydrocinchonidine From Cinchonidine by Reduction

Into a 500 c.c. Erlenmeyer flask charge $H_2O$ (168.0 g.), $H_2SO_4$(97%) (15.0 g.), cinchonidine base (40.0 g.), and palladium chloride, 2% in $H_2O$ (15.0 c.c.) with stirring (magnetic stirrer).

The air in the flask is displaced by hydrogen, with the hydrogen charged under pressure of a column of water (80–100 cm.). The hydrogenation reaction proceeds slowly until the palladium is entirely reduced. Good stirring is required.

Reduction time is about 4 hours. The reduction ceases when almost all of the theoretically required hydrogen is absorbed.

The reacted product is filtered from the palladium and then diluted with water to 600 c.c., with stirring.

The product is then charged rapidly with good agitation with about 25 g. 50% NaOH to a pH 9–10. Stirring is continued for 10 minuted. The amorphous precipitate of dihydrocinchonidine is the filtered by vacuum and washed well with water. The product is then tamped as dry as possible, and then spread out to dry in air.

Crystallization of the product is achieved from 50% ethanol-water with cooling to 0°–2° C. for 8–10 hours. The product is then filtered and washed with minimum of cold 50% ethanol, and dried at 180° F. for 4 hours.

Yield, First extraction: 31.6 g. M.P. 231° C.
Yield, Second extraction: 6.0 g. M.P. 230° C.
Total combined material: 37.6 g. — about 94% of theoretical yield.

The combined material of Example 1 may be used to prepare, by well-known art, and using one of the appropriate arids, a precursor salt such as dihydrocinchonidine sulfate which can then be reacted with additional materials to form perhalide light-polarizing materials. A process and formulation for making light-polarizing particles is set forth in Example 2.

EXAMPLE 2

Process and Formulation for Making Dihydrocinchonidine Sulfate Periodide

| Solution A | |
|---|---|
| 3.75 g. | dihydrocinchonidine sulfate |
| 20.00 g. | 2-ethoxyethanol |
| 10.00 g. | $H_2O$ |
| Solution B | |
| 10.00 g. | tricresyl phosphate (TCP) |
| 42.52 g. | of a 33⅓% solution of nitrocellulose in 2-ethoxyethanol. The nitrocellulose should be a mixture of low viscosity (18.6 cps) and high viscosity (17 second) types, 50% each. |

Mix Solution A with Solution B. This combination mixture is called Solution C.

| Solution D | | |
|---|---|---|
| | 0.49 g. | $CaI_2$ |
| | 12.00 g. | n-propanol |
| Then add | | |
| | 3.04 g. | $I_2$ |
| | 35.00 g. | TCP |
| Shake well for 15 minutes | | |

Solution C is combined with Solution D, with vigorous mixing. In less than 1 minute a product forms having a deep blue color, in a gel formation. This product, which includes a very large number of extremely small particles is sometimes referred to as a "wet paste."

Drying can be accomplished by spreading the wet paste as a film, e.g., 12 mils thick, on a glass plate, and allowing the volatile solvents in the paste to come off. For a film 12 mils thick about 3 hours is required for drying. The film in any event should be dried until there is no significant odor from it. The resulting product is sometimes called a "dry paste." Use of tricresyl phosphate (TCP), a high-boiling point plasticizer in the above formulation is optional. However, its use can facilitate the spreading of a wet paste and subsequent dispersion of a dry paste.

After drying, a paste may be dispersed into a suspending medium. To accomplish this the dry paste should first be shaken, ground, or otherwise well mixed into a suspending medium to make a suspension. Any liquid or combination of liquids which has a relatively high electrical resistivity, does not degrade or attack the particles or other components of the suspension, and which dissolves the protective colloid, e.g., nitrocellulose polymer, which is used in the suspension to stabilize it, may be employed as a suspending medium. Non-limiting examples include liquids such as esters including isopentyl acetate, dioctyl phthalate, diisodecyl adipate, and para-nonylphenyl acetate. Non-solvents for the polymer may also be used as part of the suspending medium if they do not cause the polymer to precipitate.

The suspension may, for example, be well dispersed by subjecting an undispersed mixture of dried paste and liquid suspending medium to ultrasonic agitation for a sufficiently long time, which may require in excess of 10 hours using a Bransonic 32, an ultrasonic mixer sold by the Branson Instrument Co. of Stamford, Conn. Additional liquid suspending medium or other materials may be added to the suspension after its dispersion in order to make it less concentrated or for other purposes such as altering its viscosity.

The dispersed suspension may be cleaned. One method for accomplishing this is to add to the suspension a sufficiently large quantity of a liquid that is a non-solvent for the polymeric protective colloid, so as to cause the polymer to precipitate from solution. Because the polymer is bonded to the suspended particles, the latter are also dragged out of suspension when the polymer is precipitated. For example, if the polymer is nitrocellulose, hexane can be used as the non-solvent to cause precipitation. The supernatant may be discarded and the precipitated particles and polymer resuspended in a suitable suspending medium. In such case it is usually preferable to vigorously disperse the new suspension, e.g., by ultrasonic mixing and agitation.

Particle size fractions can be selected from the suspension by conventional centrifugation methods. The relatively large particles in such a suspension can usually be removed by centrifuging at 4700 r.p.m. for about 20 minutes.

Although calcium iodide is used as the iodide in Example 2, and is preferred because the particles can be made extremely small in size, a wide choice of alternative iodides is available including, for example, KI, $NH_4I$, RbI, CsI, etc. The quantity of iodide needed when an alternative iodide is used varies somewhat from case to case depending on the molecular weight of the iodide, but can be easily estimated by conventional chemical methods from the data for $CaI_2$ given in Example 2.

The halide in the polarizing material need not be an iodide. For example, a bromide may be used. Calcium bromide, $CaBr_2$, has, for example, been found to make excellent polarizing crystals as shown in Example 3.

EXAMPLE 3

Example 2 is repeated except that 0.88 g. of $CaBr_2$ is substituted for 0.49 g. of $CaI_2$, with similar results.

Substitution of bromine atoms for an iodine atoms tends to change the spectral characteristics of the resulting polarizing particles, generally shifting them from dark blue for a periodide toward the red-brown for a perbromide, with intermediate shades expected for particles incorporating a combination of bromide and iodine, or iodide and bromine. The term "perhalide" as used herein includes all such combinations as well.

As stated previously the base material need not be cinchonidine. Examples 4, 5, 6 and 7 relate to other base materials which similarly can be reduced and further reacted and processed as aforesaid to form light-polarizing particles.

EXAMPLE 4

Example 2 is repeated, but with dihydroquinine sulfate substituted for dihydrocinchonidiene sulfate, with similar results.

EXAMPLE 5

Example 2 is repeated, but with dihydroquinidine sulfate substituted for dihydrocinchonidine sulfate, with similar results.

EXAMPLE 6

Example 2 is repeated, but with dihydrocinchonine sulfate substituted for dihydrocinchonidine sulfate, with similar results.

EXAMPLE 7

Example 2 is repeated, but with dihydrocupreine sulfate substituted for dihydrocinchonidine sulfate, with similar results.

EXAMPLE 8

Example 2 is repeated, except that dihydrocinchonidine mucate is substituted for dihydrocinchonidine sulfate, with similar results.

EXAMPLE 9

Example 2 is repeated, except that dihydrocinchonidine terephthalate is substitute for dihydrocinchonidine sulfate, and a small amount of concentrated sulfuric acid (at least 0.25 g.) is added to the reaction mixture to facilitate the reaction, with similar results.

EXAMPLE 10

Example 2 is repeated, except that dihydrocinchonidine pyromellitate is substituted for dihydrocinchonidine sulfate, and a small amount of concentrated sulfuric acid (at least 0.25 g.) is added to the reaction mixture to facilitate the reaction, with similar results.

It is to be noted that the particles are formed in a chemical environment that may include other alcohols, e.g., n-propanol and ether-alcohols, e.g., 2-ethoxyethanol. The polarizing materials of the present invention have been found to be highly stable in such environments relative to other known periodide polarizing particles and, especially, relative to the corresponding particles made from base materials that were never saturated prior to forming a precursor salt and subsequently forming a perhalide therefrom. The chemical stability of a dry paste with respect to a given solvent can be readily ascertained by mixing a specific quantity of the paste into a quantity of the solvent and observing whether a change in the color of the paste takes place and, if so, at what rate. This may be compared with the color of the paste when it is dispersed in a known non-solvent for the particles such as dioctyl phthalate (DOP) or dioctyl adipate (DOA), or a combination of DOP or DOA with a halogenated liquid such as dibromotetrafluorethane. One can test bare particles for their chemical stability by following the aforesaid test procedure after first having prepared a paste without polymer or plasticizer present. If a solvent attacks or dissolves the bare particles, a strongly tinted solution may be observed, whereas little or no tint is observed in the case of a non-solvent.

Although, as aforesaid, many different organic base materials are included within the scope of the present invention, the perhalides of dihydrocinchonidine sulfate are preferred.

In the formulation and process described in Example 2 for making dihydrocinchonidine periodide, several facts detailed in the following paragraphs are considered to be of special importance.

First, tricresyl phosphate (TCP), the plasticizer listed in Example 2, is the preferred plasticizer for the materials and suspensions of this invention, if a plasticizer is used at all, because particle sizes remain small when TCP is used whereas many other plasticizers promote unwanted particle growth which can cause light scatter and agglomeration tendencies when a suspension is placed in an activated light valve.

Second, some water should usually be present in the reaction mixture to help dissolve the precursor and in order to form crystals that polarize light effectively. In general, at least 1.5 g. of $H_2O$, and preferable at least 2.5 g. of $H_2O$ are needed in the reaction mixture per gram of precursor to produce particles of the desired quality. Furthermore, as indicated above, and shown in Solution A of Example 2, when water is used in the reaction mixture, it is best to use it to help dissolve the precursor prior to the final reaction wherein particles are produced. However, if water is so used together with the precursor, it is additionally necessary to use as a co-solvent with the water and precursor at least 1.5 g., and preferably at least 2 g. of an alcohol or ether-alcohol per gram of water, prior to reaction with other reactants, in order to prevent the water from precipitating from solution any substantially non-water soluble polymer such as nitrocellulose.

Suspensions of the light-polarizing particles of this invention have been used successfully as the working fluids in fluid suspension light valves, as previously described. Light valves can use continuous area electrodes within the active region of the cells, or the electrodes of some light valves may be formed in patterns so as to exhibit a desired display. Further, instead of allowing light to pass through the cell from front to rear, the rear surface may be made reflective so as to provide a mirror of variable reflectivity.

Although specific embodiments of the invention have been described, it will be appreciated that many modifications thereon may be made by one skilled in the art, which fall within the spirit and scope of this invention.

What is claimed is:

1. A method for forming a light-polarizing material for use in a light valve, comprising:
    (a) hydrogenating an unsaturated bond of a branch chain of an organic compound to form a saturated bond compound;
    (b) forming a salt of the compound formed in step a;
    (c) forming a perhalide of the compound of step b; and
    (d) forming a suspension of the perhalide in a liquid, wherein the suspension is light polarizing.

2. The method of claim 1, wherein the slit is formed by reaction of the saturated bond compound with an acid.

3. The method of claim 1, wherein the perhalide is formed by reaction of the compound of step b with a halide and a halogen.

4. The method of a claim 1, wherein the liquid is an ester.

5. The method of claim 1, wherein the organic compound comprises an aryl group and wherein the unsaturated bond is on a branch chain of the aryl group.

6. The method of claim 5, wherein the organic compound is an alkaloid.

7. The method of claim 5, wherein the organic compound is cinchonidine.

8. The method of claim 5, wherein the organic compound has the said saturated bond in the alpha position.

9. The method of claim 1, wherein the salt is formed by reaction with an acid taken from the group consisting of sulfuric acid and polybasic organic acids.

10. A light-polarizing material for use in a light valve comprising,
a liquid suspension of particles comprising a perhalide of an organic compound having an aryl group and a saturated branch connected to the aryl group, wherein said particles are light-polarizing in said suspension.

11. The light-polarizing material of claim 10, wherein the unsaturated form of said organic compound is an alkaloid.

12. The light-polarizing material of claim 10, wherein the unsaturated form of said organic compound is cinchonidine.

13. The light-polarizing material of claim 10, wherein the unsaturated form of said organic compound is quinine.

14. The light-polarizing material of claim 10, wherein the organic compound further comprises the addition of an acid moiety.

15. The light-polarizing material of claim 14, wherein the acid is an acid taken from the group consisting of sulfuric acid and polybasic organic acids.

16. The light-polarizing material of claim 14, wherein the acid is a hydroxy organic acid.

17. The light-polarizing material of claim 10, wherein the particles are colloidal.

18. The light-polarizing material of claim 10, wherein the liquid is an ester.

19. The light-polarizing material of claim 10, wherein the perhalide comprises a mixture of halides.

* * * * *